United States Patent
Gross

(10) Patent No.: US 11,407,901 B2
(45) Date of Patent: Aug. 9, 2022

(54) SYSTEM AND METHOD FOR PROTECTING A SURFACE FROM UV RADIATION

(71) Applicant: The Boeing Company, Chicago, IL (US)

(72) Inventor: Adam F. Gross, Santa Monica, CA (US)

(73) Assignee: THE BOEING COMPANY, Chicago, IL (US)

( * ) Notice: Subject to any disclaimer, the term of this patent is extended or adjusted under 35 U.S.C. 154(b) by 262 days.

(21) Appl. No.: 16/007,872

(22) Filed: Jun. 13, 2018

(65) Prior Publication Data

US 2019/0382597 A1    Dec. 19, 2019

(51) Int. Cl.
| | |
|---|---|
| *C09D 5/24* | (2006.01) |
| *C09D 1/00* | (2006.01) |
| *A61L 2/10* | (2006.01) |
| *C08J 7/06* | (2006.01) |
| *C09D 5/32* | (2006.01) |
| *C08J 7/043* | (2020.01) |
| *C08J 7/046* | (2020.01) |

(52) U.S. Cl.
CPC .............. *C09D 1/00* (2013.01); *A61L 2/10* (2013.01); *C08J 7/043* (2020.01); *C08J 7/046* (2020.01); *C08J 7/06* (2013.01); *C09D 5/24* (2013.01); *C09D 5/32* (2013.01)

(58) Field of Classification Search
CPC ... C09D 5/24; C09D 5/32; C09D 7/61; C09D 1/00; A61L 2/10; C08J 7/06; C08K 3/38; C08K 2003/3036; C08K 2003/2231; C08K 3/22; C08K 3/40; C08K 2003/2293; C08K 2003/2241; C08K 3/04
See application file for complete search history.

(56) References Cited

U.S. PATENT DOCUMENTS

| | | | | |
|---|---|---|---|---|
| 4,535,247 A | * | 8/1985 | Kurtz ..................... | A61L 2/24 250/436 |
| 6,342,556 B1 | * | 1/2002 | Batdorf .................. | B05D 7/08 524/432 |
| 7,754,801 B2 | * | 7/2010 | Sheerin ................... | C09D 5/32 524/236 |
| 7,923,071 B2 | * | 4/2011 | Charters ............... | B32B 15/085 427/336 |
| 9,623,133 B2 | | 4/2017 | Childress et al. | |

(Continued)

FOREIGN PATENT DOCUMENTS

| | | |
|---|---|---|
| WO | 2005095500 A1 | 10/2005 |
| WO | 2009064845 A2 | 5/2009 |

OTHER PUBLICATIONS

Corning, Corning Gorilla Glass 5, Corning Incorporated, Jul. 2016, 2 pages.

(Continued)

*Primary Examiner* — Regina M Yoo
(74) *Attorney, Agent, or Firm* — MH2 Technology Law Group LLP

(57) ABSTRACT

A method of protecting a polymer from UV degradation includes impinging ultraviolet ("UV") radiation from an artificial UV source onto an interior object, the interior object comprising: i) a polymer substrate; and ii) a continuous inorganic film on the polymer substrate. The continuous inorganic film protects the polymer substrate from the ultraviolet radiation.

31 Claims, 2 Drawing Sheets

START

IMPINGING ULTRAVIOLET ("UV") RADIATION FROM AN ARTIFICIAL UV SOURCE ONTO AN INTERIOR OBJECT, THE INTERIOR OBJECT COMPRISING: i) A POLYMER SUBSTRATE; AND ii) A CONTINUOUS INORGANIC FILM ON THE POLYMER SUBSTRATE, THE CONTINUOUS INORGANIC FILM PROTECTING THE POLYMER SUBSTRATE FROM THE ULTRAVIOLET RADIATION

END

(56) References Cited

U.S. PATENT DOCUMENTS

| | | | | |
|---|---|---|---|---|
| 2005/0260786 | A1* | 11/2005 | Yoshikawa | H01G 9/2009 438/85 |
| 2007/0154646 | A1* | 7/2007 | Bochnik | C09D 133/08 427/384 |
| 2007/0190331 | A1* | 8/2007 | Charters | B32B 27/00 428/412 |
| 2008/0213128 | A1* | 9/2008 | Rudy | A61L 2/10 422/24 |
| 2012/0282135 | A1* | 11/2012 | Trapani | A61L 2/208 422/3 |
| 2015/0303336 | A1* | 10/2015 | Lefebvre | H01L 31/048 136/259 |
| 2016/0074546 | A1* | 3/2016 | Rizzone | A61L 2/10 250/455.11 |
| 2018/0127987 | A1* | 5/2018 | Bradway | C08L 101/00 |

OTHER PUBLICATIONS

Wikipedia, List of semiconductor materials, https://en.wikipedia.org/wiki/List_of_semiconductor_materials, accessed Jun. 13, 2018, pp. 1-12.

Author Unknown, What does UV radiation actually do to degrade plastics?, United States Plastics Corp., Dec. 11, 2009, 1 page.

Author Unknown, UV Damage to Polymers, Socioeconomic Data and Applications Center, Environmental Effects of Ozone Depletion, 1998 Assessment, pp. 1-4.

Corning, Corning Willow Glass Fact Sheet, Corning Incorporated, 2017, 1 page.

Author Unknwon, Absorption of Light, http://pvcdrom.pveducation.org/SEMICON/ABSORPT.HTM, accessed May 28, 2018, 1 page.

Author Unknown, Absorption Depth, http://pvcdrom.pveducation.org/SEMICON/ABSDEPTH.HTM, accessed May 28, 2018, pp. 1-2.

Cui et al., "Highly Efficient Inorganic Transparent UV-Protective Thin-Film Coating by Low Temperature Sol-Gel Procedure for Application on Heat-Sensitive Substrates," Advanced Materials, 2008, 20, 65-68.

Extended European Search Report dated Nov. 14, 2019 in corresponding EP Application No. 1917409.8, 6 pages.

Communication pursuant to Article 94(3) EPC dated Jul. 21, 2020 in corresponding European Application No. 19179409.8, 4 pages.

Extended European Search Report issued in corresponding EP Application No. 21179428.4, 7 pages.

* cited by examiner

SYSTEM AND METHOD FOR PROTECTING A SURFACE FROM UV RADIATION

DETAILED DESCRIPTION

Field of the Disclosure

The present disclosure is directed to a system and method for protecting an object comprising a polymer from UV degradation.

Background

UV radiation from the sun is well known for causing degradation to many materials, including objects made from polymers. To protect such objects, UV protectants are often employed. Most conventional UV protectants are designed to protect from terrestrial UV radiation, between about 275 nm and about 400 nm. Current approaches to UV protection include either incorporating UV protectants into the surface to be protected, or applying a polymer coating with UV protectants or absorbers on top of the surface.

Artificial UV radiation is sometimes used for disinfecting purposes. However, UV radiation for disinfecting applications is most effective at less than or equal to 280 nm, which corresponds to the ultraviolet C spectrum ("UVC"). As discussed in more detail below, conventional UV protectant technology may not be effective for protecting against UVC radiation.

For conventional systems in which UV absorbers are incorporated into plastic or polymer surfaces, the absorbers are either: 1) organic UV absorbing molecules combined with hindered amines, 2) zinc oxide or titanium dioxide nanoparticles used in sunscreen lotions or n a polymer film that is marketed as ceramic window tint for automobiles, or 3) inorganic pigments that absorb UV radiation. However, this UV protection layer does not contain a continuous UV protectant layer. Rather, absorbers, nanoparticles, and pigments used in these systems are designed to screen out lower intensity solar based UV radiation and not the high intensity UV radiation used for sanitization or disinfection. Thus, it is not known if these types of organic UV absorbers will function at <275 nm. Furthermore, if any of the higher intensity UVC radiation penetrates through the absorbers or is absorbed by polymer/plastic between absorber molecules, nanoparticles or pigments, the underlying plastic or polymer will be damaged. Lastly, increasing the amount of the protectants in the polymer or plastic is not always feasible because 1) organic molecules will phase separate above 1-2 wt % and change the surface appearance, 2) nanoparticles will agglomerate above 20-30 wt % and change the surface's appearance due to light scattering, and 3) pigments will change the perceived polymer color as the pigment level is increased, which is often not desirable. High levels of fillers will also make the polymer very brittle and crack.

In other conventional UV protection systems, a transparent UV protection film comprising UV absorbing molecules or particles in a polymer matrix material may be applied over a surface. This film/coating protects the surface from UV damage by absorbing all of the UV radiation using, for example, organic UV absorbing molecules combined with hindered amines or zinc oxide or titanium oxide nanoparticles described above. However, this approach only works if the polymer matrix material is UV transparent and does not absorb UV radiation and photodarken. Unfortunately, many polymers absorb UV radiation in the UVC region and thus will photodarken from exposure if exposed to UVC radiation.

In fields that are generally unrelated to UV protection, transparent, continuous inorganic coatings are applied for corrosion protection and wear resistance on tools, home appliances (faucets, appliance fronts, handles), surgical tools, and moving mechanical parts (gears, cylinder heads). For example, it is known to physically vapor deposit a nitride layer, such as a TiN film, on metal faucets to prevent corrosion and water spots. However, these coatings are not generally known for UV protection of polymer materials. Furthermore, TiN is not transparent to visible light.

Thus, novel films for protecting polymer containing objects from UV radiation used in sanitization, which has wavelengths of less than or equal 280 nm, would be considered a step forward in the art.

SUMMARY

The present disclosure is directed to a method of protecting a polymer from UV degradation. The method comprises impinging ultraviolet ("UV") radiation from an artificial UV source onto an interior object, the interior object comprising: i) a polymer substrate; and ii) a continuous inorganic film on the polymer substrate. The continuous inorganic film protects the polymer substrate from the ultraviolet radiation.

The present disclosure is also directed to a UV radiation disinfection system. The UV radiation disinfection system comprises: an interior object comprising: i) a polymer substrate; and ii) a continuous inorganic film on the polymer substrate. The UV radiation disinfection system also comprises an artificial UV source directed so as to impinge ultraviolet ("UV") radiation onto the interior object when the artificial UV source is powered on. The artificial UV source is designed to emit radiation at a UVC wavelength suitable for disinfection. The continuous inorganic film has a property of absorbing UV radiation at the UVC wavelength.

The present disclosure is also directed to an interior object. The interior object comprises a polymer substrate and a continuous inorganic film on the polymer substrate. The continuous inorganic film has a property of absorbing UV radiation at a UVC wavelength suitable for disinfection.

The present disclosure is also directed to a method comprising coating a continuous inorganic film on a polymer substrate. The continuous inorganic film has a property of absorbing UV radiation at a UVC wavelength suitable for disinfection.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrates aspects of the present teachings and together with the description, serve to explain the principles of the present teachings.

Figure 1:
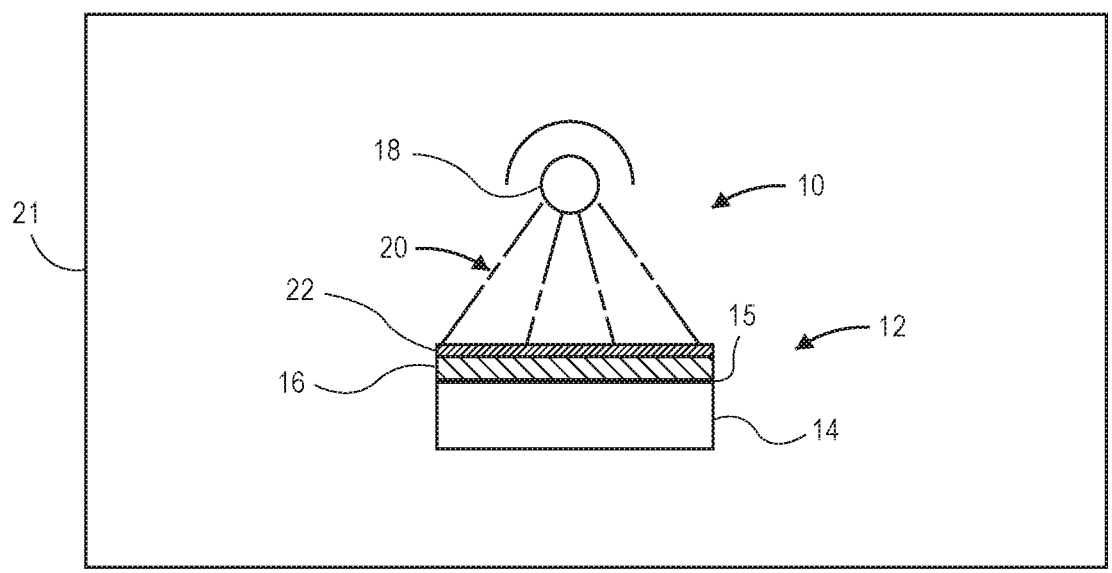
FIG. 1 illustrates a UV radiation disinfection system, according to the present disclosure.

It should be noted that some details of the figures have been simplified and are drawn to facilitate understanding rather than to maintain strict structural accuracy, detail, and scale.

DESCRIPTION

Reference will now be made in detail to the present teachings, examples of which are illustrated in the accompanying drawings. In the drawings, like reference numerals have been used throughout to designate identical elements. In the following description, reference is made to the accompanying drawings that form a part thereof, and in which is shown by way of illustration specific examples of practicing the present teachings. The following description is, therefore, merely exemplary.

UVC radiation, which includes wavelengths ranging from 180 nm to 280 nm, has been found to be highly effective for disinfecting surfaces where bacteria are problematic, such as, for example, lavatory surfaces in aircraft, or other such surfaces, as will be described herein below. The surfaces being disinfected often comprise polymers. Applicants have found that when repeatedly used to disinfect these polymer surfaces, UVC radiation can cause the polymer surface to become discolored and potentially degrade, or crack. The present disclosure provides a solution to these problems, which includes protecting the polymer surfaces exposed to UVC radiation with a continuous inorganic film. The continuous inorganic film absorbs UVC radiation and thereby reduces or prevents degradation to the underlying polymer substrate. This solution and other technical effects are described in detail below.

Referring to FIG. 1, the present disclosure is directed to a UV radiation disinfection system 10. The system comprises an interior object 12 comprising a polymer substrate 14. A continuous inorganic film 16 is disposed on the polymer substrate 14. An artificial UV source 18 is directed so as to impinge ultraviolet ("UV") radiation 20 onto the interior object 12 when the artificial UV source 18 is powered on. The artificial UV source 18 is designed to emit radiation at a UVC wavelength suitable for disinfection, such as wavelengths ranging from about 180 nm to about 280 nm. The continuous inorganic film 16 has the property of absorbing UV radiation at the UVC wavelength the artificial UV source 18 is designed to emit, thereby protecting the polymer substrate 14 from the UV radiation.

The interior object 12 can be any object that comprises a polymer substrate 14 that is likely to be exposed to UV radiation. In an implementation of the present disclosure, the interior object 12 can be positioned in a structure 21. Structure 21 can be indoors, for example, in a building or a vehicle where UV radiation may be employed for disinfection purposes, such as a lavatory or food preparation area in any one of an aircraft, a spacecraft, a public or private building, a bus, a boat such as a cruise ship, submarine and so forth, a rail car or a recreational vehicle. Examples of interior object 12 can include any object that is indoors, such as a wall, counter, sink, handle, faucet, toilet, appliance or floor or any other object comprising a polymer surface for which UV protection is desired. The polymer substrate 14 can be any portion of the interior object 12 and can make up any percentage of the interior object by weight. For example, the polymer substrate (including any inorganic or organic fillers employed in the polymer substrate) can comprise 1% to 100% of the interior object by weight, not counting the weight of the continuous inorganic film 16 or mechanical reinforcements, such as wire mesh or metal bars, in the polymer substrate.

The polymer substrate 14 can comprise any suitable polymer that absorbs UVC radiation. For purposes of this application, a polymer is an organic macromolecule composed of many repeated monomer units, such as more than a 10,000, repeating monomer units, such as 10,000 to 1 E+100, or more monomer units, or 100,000 to 100,000,000 monomer units. The upper limit of the number of monomer units is only limited by the size of the polymer substrate, and so could potentially be practically limitless. Examples of polymers include epoxies, polyurethanes, polyethylene, polypropylene, Polyethylene terephthalate (PET), Polyether ether ketone (PEEK), polyetherketoneketone (PEKK), Acrylonitrile butadiene styrene (ABS), polyvinylchloride (PVC), thermoplastic olefins (TPO), polytetrafluoroethylene (e.g., Teflon), polyvinylfluoride (PVF) and silicones, or any combination thereof. A commercial example of a PVF polymer is TEDLAR®, which is made by E. I. du Pont de Nemours and Company of Wilmington, Del.

If not protected, the polymer substrate 14 absorbs the UVC radiation. The absorption of light is the result of optically exciting a chemical bond in the polymer. Absorption of UVC radiation can result in discoloration (referred to herein as photodarkening) and other types of degradation, such as cracking. Such degradation to the polymer may occur over time if the polymer absorbs, for example, 1-2% to 100% of the incident UVC radiation, such as 10% to 100%.

To reduce or prevent such degradation, a continuous inorganic film is employed over the polymer substrate to block the UVC radiation. The continuous inorganic film can be any semiconductor or insulator that absorbs UV radiation at the UVC wavelength the artificial UV source 18 is designed to emit. If a semiconductor material is employed as the continuous inorganic film, the semiconductor has a bandgap that is greater than 3.1 eV and will absorb light with energy above that bandgap. The 3.1 eV minimum is chosen so the semiconductor layer is visibly transparent. The upper limit of the semiconductor bandgap is less than the energy of the UV radiation source, such as less than or equal to 6.9 eV, or about 6.2 eV. Examples of suitable semiconductor materials can be chosen from Group IV semiconductors, Group II-VI semiconductors, Group III-V semiconductors, metal phosphide semiconductors, metal nitride semiconductors, metal sulfide semiconductors and metal oxide semiconductors that have the desired bandgap. Specific examples include diamond, lithium niobite, tin dioxide, nickel(II) oxide, zinc sulfide, boron arsenide, gallium nitride, silicon carbide, such as 4H—SiC, zinc oxide, titanium dioxide, such as anatase, fluorinated tin oxide, indium tin oxide, and mixtures thereof. In an implementation, the semiconductor materials are chosen from silicon carbides, such as 4H—SIC, zinc sulfide and gallium nitride.

Insulating materials employed as the continuous inorganic film can be any electrically conductive material that absorbs UVC radiation, including light at wavelengths in any of the UVC ranges discussed herein. In implementations where the continuous inorganic film is an insulator, the insulator can be chosen, for example, from diamond-like carbon, indium oxide, chromium nitride, borosilicate glass, and borosilicate-lime glass. Commercially available glass includes, for example, Gorilla Glass® and Willow Glass®, which are both made by Corning Inc. of Corning, N.Y., as well as Pyrex® (which is a borosilicate glass). Gorilla Glass® is an Aluminosilicate glass comprising one or more, such as all four, of silicon dioxide, aluminum, magnesium, and sodium. Willow Glass® is an Alkali-free Borosilicate glass.

The term "continuous" in the phrase "continuous inorganic film" indicates that the film is not made of discrete, inorganic particles, but instead is a sheet of material that covers at least 90%, such as 90% to 100%, of a surface area of the interior object that is exposed to the UV radiation. inorganic films are employed instead of organic films because, if used, organic films are likely to photodarken over time.

As is well understood in the art, the UV absorption of a film can generally depend on the thickness of the film. The continuous inorganic film can have any suitable thickness that provides the desired UV absorption. Example ranges of suitable thicknesses are from about 10 nm to about 2 mm, or about 30 nm to about 1 mm, or about 50 nm to about 500 microns, or about 100 nm to about 200 microns. The continuous inorganic film within these ranges of thicknesses can absorb, for example, from about 50% to about 100% of the UV radiation, such as about 70% to about 100%, about 80% to 100%, or about 90% to about 100% of the UV radiation, where the UV radiation has wavelengths within ranges of from about 180 nm to about 280 nm, such as about 200 nm to about 280, or about 200 nm to about 270 nm, or about 200 nm to about 250 nm. Additionally, the continuous inorganic film can be transmissive to visible light. For example, the continuous inorganic film transmits about 60% or more, such as about 80% to 100% of radiation in the visible spectrum of 400 nm to 800 nm. In an implementation, the continuous inorganic film 16 appears substantially clear, or transparent, so that the underlying polymer substrate 14 can be seen with the human eye when viewed through the continuous inorganic film 16. The continuous inorganic film can be smooth, or roughened to reduce gloss, if desired. Techniques for measuring the amount of UV radiation absorbed by a film are well known. For instance, a standard technique is to measure the transmission with a two beam UV/VIS/NIR spectrometer. A 100% transmission spectrum with no sample in the spectrometer baseline is first collected. Then the sample is placed in the sample holder and the amount of transmission is compared between the beam containing a sample and the beam without the sample. This same technique can be used for measuring the transmissivity of a material for radiation in the visible spectrum.

The continuous inorganic films of the present disclosure can provide one or more of the following: reduction or prevention of UV damage to an underlying polymer layer compared to the same underlying polymer layer exposed to the same UV radiation without the continuous inorganic film; reduction or prevention of discoloration of underlying polymer layers due to UV damage compared to the same underlying polymer layer exposed to the same UV radiation without the continuous inorganic film; and improved scratch resistance compared to the same underlying polymer layer without the continuous inorganic film.

In an implementation of the present disclosure, the interior object can further comprise an optional adhesion layer 15 between the polymer substrate 14 and the continuous inorganic film 16. Examples include adhesion layers comprising a material chosen from chromium, titanium, or a mixture thereof. The thickness of the adhesion layer 15 can be any suitable thickness, such as, for example, from 1 nm to 10 nm. Example techniques for making such adhesion layers include sputtering or other deposition techniques that are well known in the art.

In an implementation of the present disclosure, the interior object further comprises an optional barrier layer 22 disposed over the continuous inorganic film. The barrier layer 22 comprises any suitable material that is impervious to water or other possible contaminants. Examples of suitable materials include silicon oxide glass, aluminum nitride, boron nitride, and any combination thereof. Any other inorganic materials having a band gap that is greater than the energy of incident UV radiation can be employed. For example, the band gap can be greater than 3.1 eV, such as ranging from 3.1 eV to about 6.1 eV, or about 3.3 eV to about 5.9 eV. While barrier layer 22 can be employed over any continuous inorganic films described above, it may be particularly useful for protecting continuous inorganic films that potentially absorb water, such as any of the semiconductor materials described above.

The artificial UV source 18 emits radiation having a wavelength ranging from about 180 nm to about 280 nm. For example, the artificial UV source emits radiation having a wavelength ranging from about 200 nm to about 280 nm, or about 200 nm to about 250 nm, or about 200 nm to about 230 nm. In an example, the UV source only emits radiation ranging from about 180 nm to about 280 nm. In an example, the UVC radiation is monochromatic or substantially monochromatic, where substantially monochromatic is defined as radiation where at least 85% of the radiation is at a specified wavelength (e.g., 222 nm for a KrCl excimer bulb). Monochromatic and substantially monochromatic UV sources are well known in the art, and include, for example, LEDs that emit UV radiation. Excimer bulbs and some Hg low pressure bulbs. The range of wavelengths of from about 180 nm to about 280 nm can provide certain benefits. For example, wavelengths of 280 nm and below are known for reducing or eliminated microbes. For instance, wavelengths of about 260 to about 280 nm are known to damage microbe's DNA, while wavelengths of less than 240 nm are known to damage proteins in microorganisms. Further, ozone, which is generally considered undesirable, is made by sources with energy of less than 200 nm, so that sources of 200 nm and above may be desirable in some circumstances. Wavelengths in the range of about 200 nm to about 230 nm may have additional benefits. For instance, a study at Columbia University has shown that wavelengths in this range (e.g., at 207 nm and 222 nm) have less effect on human cells than 254 nm Hg sources.

The radiant intensity of the UV radiation at the surface on which the radiation impinges can be any suitable intensity that can provide the desired disinfection. For example, the radiant intensity can range from about 0.1 to 30 milliwatts/$cm^2$, such as 0.5 to about 20 milliwatts/$cm^2$, such as about 1 to about 10 milliwatts/$cm^2$, such as about 2 to about 5 milliwatts/$cm^2$. Light at the above listed wavelengths and intensities can be useful for eliminating or reducing microbes, such as bacteria, on surfaces.

The artificial UV source 18 can be any known or later developed UV source that emits UVC radiation at the desired wavelengths. Examples of known suitable light sources include UVC LEDs and Mercury fluorescent bulbs (also referred to as Hg vapor lamps). LEDs have wavelengths as low as about 230 nm and as high as about 280 nm. Mercury fluorescent bulbs emit radiation at wavelengths of about 254 nm. Still other UVC sources and their associated wavelengths include Krypton Iodide (KrI) excimer lamps (190 nm), Argon Fluoride (ArF) excimer lamps (193 nm), Krypton Bromide (KrBr) excimer lamps (207 nm), Krypton Bromide (KrCl) excimer lamps (222 nm), Krypton Fluoride (KrF) excimer lamps (248 nm), Xenon Iodide (XeI) excimer lamps (253 nm), Chloride (Cl2) excimer lamps (259 nm) and Xenon Bromide (XeBr) excimer lamps (282 nm). The same technical effects discussed above that are associated with the radiation wavelengths of about 180 nm to about 280 nm are also associated with these UVC radiation sources, all of which emit radiation in this range of wavelengths. For instance, the KrCl excimer lamps, which emit at about 222 nm, and the KrBr excimer lamps, which emit at 207 nm, have the technical effect of causing less damage to human cells than cancer causing 254 nm Hg sources, as discussed above, as well as the benefits of eliminating or reducing microbes without causing substantial amounts of ozone (e.g., less than 0.1 ppm by mole ozone as set forth in the National Institute for Occupational Safety and Health standards).

Figure 3:
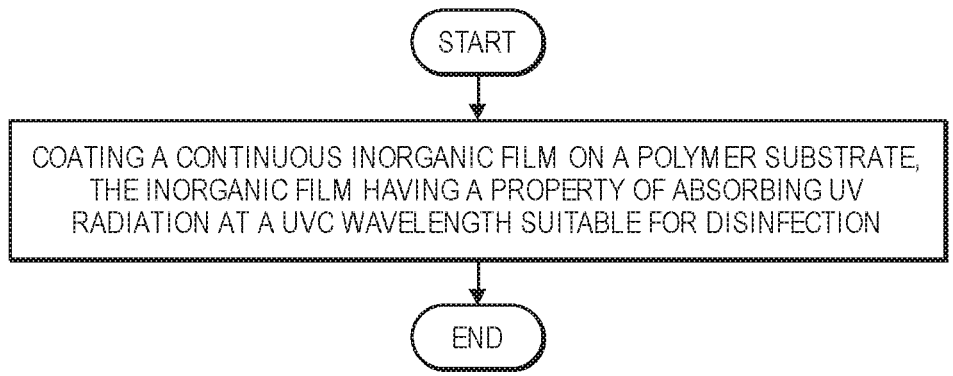
FIG. 3 illustrates a method comprises coating a continuous inorganic film on a polymer substrate, according to the present disclosure.

The present disclosure is also directed to a method of making the continuous inorganic film. As illustrated in FIG. 3, the method comprises coating a continuous inorganic film on a polymer substrate. Any of the continuous inorganic films described herein can be coated using any suitable coating method that is known or hereinafter developed. Examples of suitable coating methods include gas or liquid coating techniques, such as physical vapor deposition, chemical vapor deposition, sputtering, spray pyrolysis, plasma coating, dip coating and laminating. The continuous inorganic film can be formed on the polymer substrate, or alternatively, the continuous inorganic film can be separately formed and then attached to the polymer substrate, such as by pre-forming a glass layer (e.g., borosilicate glass or any of the other glass materials described as being suitable herein) and then laminating the pre-formed glass layer to the polymer substrate. The resulting inorganic film has the property of absorbing UV radiation at a UVC wavelength suitable for disinfection, such as at any of the wavelengths described herein.

The methods of the present disclosure can be for applying the continuous inorganic film to the polymer substrate for the first time. Alternatively, the method of making the inorganic film can be a process where the coating replenishes a continuous inorganic film already present on the polymer substrate that has at least partially worn off or otherwise lost its effectiveness for UV protection. For example, the coating to replenish the continuous inorganic film can occur after the polymer substrate is installed in a vehicle, such as any of the vehicles described herein.

Figure 2:
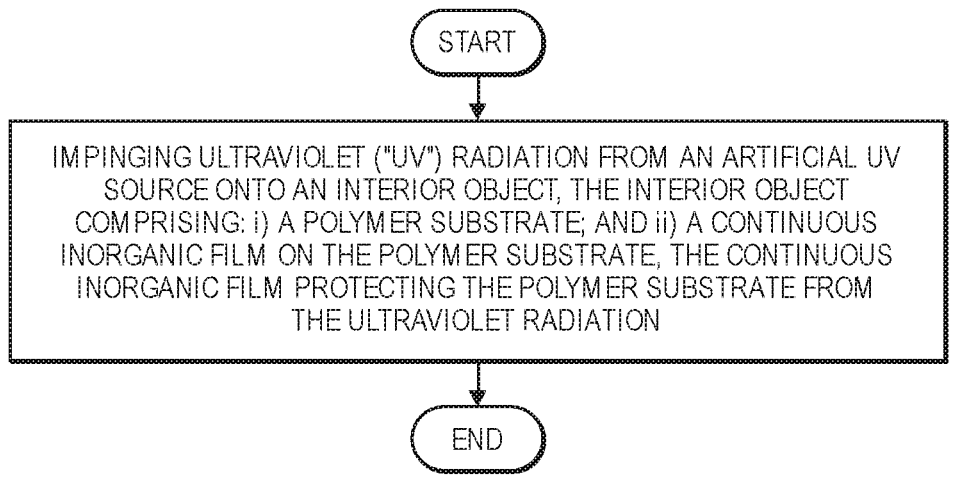
FIG. 2 illustrates a method comprising impinging ultraviolet ("UV") radiation, such as UVC radiation employed in a system for disinfecting a surface, from an artificial UV source onto an interior object, according to the present disclosure.

The present disclosure is also directed to a method of protecting a polymer from UV degradation. As shown in FIG. 2, the method comprises impinging ultraviolet ("UV") radiation, such as UVC radiation employed in a system for disinfecting a surface, from an artificial UV source onto an interior object. The interior object comprises a continuous inorganic film disposed on a polymer substrate, where the continuous inorganic film acts to protect the polymer substrate from the ultraviolet radiation. The interior object can be any of the interior objects described herein. The continuous inorganic film can be any of the continuous inorganic films described herein.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the intended purpose described herein. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A method of protecting a polymer from UV degradation, the method comprising:
impinging ultraviolet ("UV") radiation from an artificial UV source onto an interior object, the interior object comprising: i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, with the proviso that the continuous inorganic semiconductor film is not a metal oxide semiconductor film, and wherein the artificial UV source emits radiation having a wavelength ranging from about 180 nm to about 280 nm.

2. The method of claim 1, wherein the artificial UV source only emits radiation at wavelengths ranging from about 180 nm to about 280 nm.

3. The method of claim 1, wherein the artificial UV source is a UVC LED, an Hg vapor lamp, or an excimer lamp.

4. The method of claim 1, wherein the interior object is indoors and is a wall, counter, sink, handle, faucet, toilet, appliance, or floor.

5. The method of claim 1, wherein the polymer substrate comprises a polymer chosen from epoxies, polyurethanes, polyethylene, polypropylene, Polyethylene terephthalate (PET), Polyether ether ketone (PEEK), polyetherketoneketone (PEKK), Acrylonitrile butadiene styrene (ABS), polyvinylchloride (PVC), thermoplastic olefins (TPO), polytetrafluoroethylene, polyvinylfluoride (PVF), and silicones, or any combination thereof.

6. The method of claim 1, wherein the continuous inorganic film is an insulator, and the insulator is chosen from diamond-like carbon, indium oxide, chromium nitride, aluminosilicate glass, borosilicate glass, and borosilicate-lime glass.

7. The method of claim 1, wherein the continuous inorganic film has a thickness ranging from about 10 nm to about 2 mm.

8. The method of claim 1, wherein the continuous inorganic film absorbs from 90% to 100% of the UV radiation having a wavelength ranging from about 200 nm to about 280 nm and transmits about 80% to 100% of radiation having a wavelength ranging from 400 nm to 800 nm.

9. The method of claim 1, wherein the continuous inorganic film covers at least 90% of a surface area of the interior object that is exposed to the UV radiation.

10. The method of claim 1, wherein the interior object further comprises a barrier layer over the continuous inorganic film.

11. The method of claim 1, wherein the interior object further comprises an adhesion layer between the polymer substrate and the continuous inorganic film.

12. The method of claim 1, wherein the interior object is positioned in any one of an aircraft, a spacecraft, a bus, a boat, a rail car, a recreational vehicle, and a building.

13. A method of protecting a polymer from UV degradation, the method comprising:
impinging ultraviolet ("UV") radiation from an artificial UV source onto an interior object, the interior object comprising: i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, wherein the interior object further comprises an adhesion layer between the polymer substrate and the continuous inorganic film, and wherein the artificial UV source emits radiation having a wavelength ranging from about 180 nm to about 280 nm.

14. A method of protecting a polymer from UV degradation, the method comprising:
impinging ultraviolet ("UV") radiation from an artificial UV source onto an interior object, the interior object comprising: i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, wherein the interior object further comprises a barrier layer over the continuous inorganic film, and wherein the artificial UV source emits radiation having a wavelength ranging from about 180 nm to about 280 nm.

15. A method of protecting a polymer from UV degradation, the method comprising:
impinging ultraviolet ("UV") radiation from an artificial UV source onto an interior object, the interior object comprising: i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, the continuous inorganic semiconductor film being chosen from Group IV semiconductor films, Group II-VI semiconductors films, Group III-V semiconductor films, metal phosphide semiconductor films, metal nitride semiconductor films and metal sulfide semiconductor films, with the proviso that the Group II-VI semiconductor film is not a zinc oxide film, wherein the artificial UV source emits radiation having a wavelength ranging from about 180 nm to about 280 nm.

16. The method of claim 15, wherein the artificial UV source only emits radiation at wavelengths ranging from about 180 nm to about 280 nm.

17. The method of claim 15, wherein the artificial UV source is a UVC LED, an Hg vapor lamp, or an excimer lamp.

18. The method of claim 15, wherein the interior object is indoors and is a wall, counter, sink, handle, faucet, toilet, appliance, or floor.

19. The method of claim 15, wherein the polymer substrate comprises a polymer chosen from epoxies, polyurethanes, polyethylene, polypropylene, Polyethylene terephthalate (PET), Polyether ether ketone (PEEK), polyetherketoneketone (PEKK), Acrylonitrile butadiene styrene (ABS), polyvinylchloride (PVC), thermoplastic olefins (TPO), polytetrafluoroethylene, polyvinylfluoride (PVF), and silicones, or any combination thereof.

20. The method of claim 15, wherein the continuous inorganic film has a thickness ranging from about 10 nm to about 2 mm.

21. The method of claim 15, wherein the continuous inorganic film absorbs from 90% to 100% of the UV radiation having a wavelength ranging from about 200 nm to about 280 nm and transmits about 80% to 100% of radiation having a wavelength ranging from 400 nm to 800 nm.

22. The method of claim 15, wherein the continuous inorganic film covers at least 90% of a surface area of the interior object that is exposed to the UV radiation.

23. The method of claim 15, wherein the interior object is positioned in any one of an aircraft, a spacecraft, a bus, a boat, a rail car, a recreational vehicle, and a building.

24. The method of claim 15, wherein the continuous inorganic semiconductor film is chosen from Group IV semiconductor films, Group III-V semiconductor films, metal phosphide semiconductor films, metal nitride semiconductor films and metal sulfide semiconductor films.

25. A method of protecting a polymer from UV degradation, the method comprising:
impinging ultraviolet ("UV") radiation from an artificial UV source onto an interior object, the interior object comprising: i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, wherein the continuous inorganic semiconductor film comprises a material chosen from diamond, lithium niobite, tin dioxide, nickel(II) oxide, zinc sulfide, boron arsenide, gallium nitride, silicon carbide, 4H-SiC, fluorinated tin oxide, indium tin oxide and mixtures thereof, and wherein the artificial UV source emits radiation having a wavelength ranging from about 180 nm to about 280 nm.

26. The method of claim 25, wherein the continuous inorganic semiconductor film comprises a material chosen from diamond, lithium niobite, zinc sulfide, boron arsenide, gallium nitride, silicon carbide, and 4H-SiC.

27. A method of protecting a polymer from UV degradation, the method comprising:
impinging ultraviolet ("UV") radiation having a wavelength ranging from about 180 nm to about 280 nm from an artificial UV source onto an interior object, the interior object comprising:

i) a polymer substrate; and ii) a continuous inorganic film on the polymer substrate, the continuous inorganic film protecting the polymer substrate from the ultraviolet radiation, wherein the continuous inorganic film is a continuous inorganic semiconductor film having a bandgap that is greater than 3.1 eV and less than or equal to 6.9 eV, and wherein the interior object is indoors and is a wall, counter, sink, handle, faucet, toilet, appliance, or floor, wherein the continuous inorganic semiconductor film comprises a material chosen from diamond, lithium niobite, tin dioxide, nickel(II) oxide, zinc sulfide, boron arsenide, gallium nitride, silicon carbide, 4H-SiC, fluorinated tin oxide, indium tin oxide and mixtures thereof.

28. The method of claim 27, wherein the artificial UV source only emits radiation at wavelengths ranging from about 180 nm to about 280 nm.

29. The method of claim 27, wherein the artificial UV source is a UVC LED, an Hg vapor lamp, or an excimer lamp.

30. The method of claim 27, wherein the polymer substrate comprises a polymer chosen from epoxies, polyurethanes, polyethylene, polypropylene, Polyethylene terephthalate (PET), Polyether ether ketone (PEEK), polyetherketoneketone (PEKK), Acrylonitrile butadiene styrene (ABS), polyvinylchloride (PVC), thermoplastic olefins (TPO), polytetrafluoroethylene, polyvinylfluoride (PVF), and silicones, or any combination thereof.

31. The method of claim 27, wherein the continuous inorganic film absorbs from 90% to 100% of the UV radiation having a wavelength ranging from about 200 nm to about 280 nm and transmits about 80% to 100% of radiation having a wavelength ranging from 400 nm to 800 nm.

* * * * *